United States Patent [19]

Galat

[11] Patent Number: 5,811,125
[45] Date of Patent: Sep. 22, 1998

[54] NATURAL LAXATIVE

[76] Inventor: Alexander Galat, 126 Buckingham Rd., Yonkers, N.Y. 10701

[21] Appl. No.: 705,992

[22] Filed: Aug. 30, 1996

[51] Int. Cl.$^6$ .................................................. A61K 31/74
[52] U.S. Cl. ......................... 424/489; 424/439; 426/615; 426/629; 426/648
[58] Field of Search ................ 424/78.01, 455, 424/489, 195.1; 514/892; 426/615, 629, 648

[56] References Cited

U.S. PATENT DOCUMENTS

| | | | |
|---|---|---|---|
| 4,223,023 | 9/1980 | Furda | 424/180 |
| 4,511,561 | 4/1985 | Madaus et al. | 424/195.1 |
| 5,232,699 | 8/1993 | Colliopoulos | 424/195.1 |
| 5,397,573 | 3/1995 | Kajs et al. | 424/451 |
| 5,422,100 | 6/1995 | Eliaz et al. | 424/70.11 |
| 5,516,524 | 5/1996 | Kais et al. | 424/439 |
| 5,525,355 | 6/1996 | Brown et al. | 424/456 |

*Primary Examiner*—Thurman K. Page
*Assistant Examiner*—Kathryne E. Shelborne
*Attorney, Agent, or Firm*—Bryan, Levitin & Bab, LLP

[57] ABSTRACT

A medicine for relieving constipation, the medicine having an effective dose of the edible portion of the caraway plant. The effective dose is combined with filler agents, or in one embodiment, with a bulk-producing agent to increase the effectiveness of the laxative, in an orally ingestible form. The medicine is gentle-acting, natural and has no known adverse side-effects associated with its use. A method for using the medicine is also provided.

4 Claims, No Drawings

NATURAL LAXATIVE

FIELD AND BACKGROUND OF THE INVENTION

The present invention relates to a new laxative compound, and in particular to a laxative compound containing caraway which is effective yet gentle in its action on the human digestive system.

Constipation is the most common chronic digestive problem occurring in humans. It is estimated that over five million people suffer from frequent constipation, and that almost one billion dollars is spent annually on laxative products.

A common cause of this problem is the weakening of the colon and intestines of humans with age. Normal intestinal contractions (peristalsis) weaken, and food is not properly moved through the digestive tract, resulting in constipation.

There are many known laxatives for curing the problem of constipation. Some of these products use synthetic chemical compounds such as phenolphthalein (EX-LAX, CORRECTOL) and biscodil (DULCOLAX, CARTER'S PILLS). Others have milk of magnesia, castor oil, mineral oil, or herbal extracts, other than caraway, as their active ingredient. These laxative products fail to provide a satisfactory solution to the problem of chronic constipation. These chemicals have many undesirable, and sometimes dangerous, side-effects. In particular, they severely irritate the lining of the intestine and colon producing intestinal cramps, pain and nausea.

Laxative products with more gentle action have psyllium and calcium polycarbophil as an active ingredient. Examples of these products include METAMUCIL, FIBER-CON, and SERUTAN. The psyllium and calcium polycarbophil compounds are bulk-producing agents. They are intended to replace or supplement the bulk-producing effect of foods such as fruits and vegetables, which are often lacking in older people's diets. However, these products are only truly effective in cases of mild to moderate constipation. And, bulk-producing agents are even less effective when the constipation is due to the weakening of the intestines and colon, as they cannot produce sufficiently strong peristalsis to alleviate the condition.

Natural laxatives which are commercially available, such as Sandoz' GENTLE NATURE, or SmithKline Beecham's NATURE'S REMEDY, rely upon a family of chemical compounds to activate the laxative action of the product. The chemical compounds, called anthraquinones, are combined with aloe, senna, cascara sagrada, and other plants. Anthraquinones, however, trigger very strong intestinal contractions, and when used in large doses can cause severe cramps. They have also been linked to kidney damage. As the use of progressively larger doses of laxative to relieve constipation is common, laxatives tend to lose effectiveness over time since tolerance to the active chemicals is raised. Thus the problems associated with anthraquinones are often suffered by users of these products.

SUMMARY OF THE INVENTION

It is an object of the present invention to provide a new laxative which is gentle, yet effective in relieving chronic constipation, especially in cases where the condition is caused by weakened intestinal and colon walls.

Accordingly, a laxative product containing the edible portion of the plant *Carum carvi*, or caraway seeds. The product may be combined in oil or powder form with conventional inactive filler ingredients to form a pill, which may be ingested by a person suffering from constipation.

The action of this natural laxative, which requires no additional chemicals to activate its beneficial properties, is gentle and stimulates the muscles of the intestine and colon to improve peristalsis and relieve constipation.

When caraway seeds are combined with bulk-producing agents, such as psyllium or calcium polycarbophil, the laxative is even more effective, but does not lose its gentle action. The bulk-producing agents help the digestion and processing of foods in the intestines, making the peristalsis stimulated by caraway seeds more effective.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter in which a preferred embodiment of the invention is illustrated.

DETAILED DESCRIPTION OF THE PREFERRED EMBODIMENT

The laxative of the invention is made by combining the edible portion of the *Carum carvi* plant, or caraway seeds, with inactive filler ingredients to form an orally ingestible medicine. The caraway may be mixed in oil or powder form with the filler ingredients, and any known form of orally ingested medicine is acceptable for use, including, but not limited to, tablets, capsules, coated tablets, and liquid suspensions.

The suggested effective dosage for a human adult is 500 mg. To help minimize the size of the medicine delivery unit, caraway extract may be used to make the medicine. The extract can be concentrated in oil form.

When used to treat constipation, the 500 mg of active caraway is ingested by a patient. The natural effect of caraway on the human body is to stimulate and produce peristalsis in the intestines and colon. The resulting peristalsis effectively moves food through the patient's digestive tract and colon, thus relieving the constipated condition without causing unnecessary pain or discomfort to the patient.

This laxative medicine can be used more effectively to treat chronic constipation because it has no known undesirable side-effects.

In an embodiment of the laxative, which has improved effectiveness, a bulk-producing agent is combined with the caraway and filler ingredients to form the orally ingestible medicine. The bulk-producing agent causes the intestinal contents to combine in larger quantities within the intestinal tract. Then, when caraway-stimulated peristalsis occurs, it is more effective, as there is a larger mass of intestinal contents moving through the intestine to the colon. Thus, even smaller contractions of the intestine will be more effective in moving the wastes and relieving the constipated condition of the patient.

While a specific embodiment of the invention has been described in detail to illustrate the application of the principles of the invention, it will be understood that the invention may be embodied otherwise without departing from such principles.

What is claimed is:

1. A method of relieving a condition of constipation in a human patient, comprising:

providing a medicine, the medicine having an effective dose of caraway seeds in an orally ingestible form;

ingesting the medicine by the human patient; and permitting the medicine to stimulate a peristaltic action in a digestive tract of the human patient for moving digestive track contents through the tract.

2. A method of relieving a condition of constipation according to claim 1, wherein the effective dose comprises 500 mg of caraway seed powder.

3. A method of relieving a condition of constipation according to claim 1, wherein the effective dose of caraway seeds comprises an effective dose of concentrated caraway extract.

4. A method of relieving a condition of constipation according to claim 1, wherein the medicine further comprises a bulk-producing agent, and the method further comprises allowing the bulk-producing agent to form larger masses of the intestinal contents within the digestive tract for moving through the tract.

* * * * *